US007473900B2

(12) United States Patent
Vija

(10) Patent No.: US 7,473,900 B2
(45) Date of Patent: Jan. 6, 2009

(54) ACQUISITION WINDOW COMPENSATION FOR NUCLEAR MEDICAL IMAGE RECONSTRUCTION ATTENUATION COEFFICIENT MAPS

(75) Inventor: A Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 131 days.

(21) Appl. No.: 11/454,323

(22) Filed: Jun. 16, 2006

(65) Prior Publication Data

US 2006/0284098 A1 Dec. 21, 2006

Related U.S. Application Data

(60) Provisional application No. 60/691,335, filed on Jun. 16, 2005.

(51) Int. Cl.
*G01T 1/166* (2006.01)
(52) U.S. Cl. .................................. 250/363.04
(58) Field of Classification Search ............ 250/363.04
See application file for complete search history.

(56) References Cited

U.S. PATENT DOCUMENTS

2005/0058259 A1* 3/2005 Vija et al. ................ 378/210

OTHER PUBLICATIONS

Kalki et al., "Myocardial Perfusion Imaging With a Correlated X-ray CT and SPECT System: An Animal Study", IEEE TNS, 43(3), 1996, pp. 2000-2007.
White et al., "Calculated Attenuation and Energy Absorption Coefficients for ICRP Reference Man (1975) Organs and Tissues", Health Physics, 33, pp. 73-81, 1977.

* cited by examiner

*Primary Examiner*—Constantine Hannaher
(74) *Attorney, Agent, or Firm*—Peter L. Kendall

(57) ABSTRACT

Generation of attenuation maps for nuclear medicine image reconstructions based on the use of anatomical image data, such as CT data, take into account variations caused by variations in acquisition energy width and emission energy of the radioisotope used in the clinical imaging procedure, as coefficient correction factors that are stored together with such maps.

18 Claims, 4 Drawing Sheets

ACQUISITION WINDOW COMPENSATION FOR NUCLEAR MEDICAL IMAGE RECONSTRUCTION ATTENUATION COEFFICIENT MAPS

CROSS-REFERENCE TO RELATED APPLICATIONS AND CLAIM FOR PRIORITY

This application claims priority under 35 U.S.C. § 119(e) from copending U.S. Provisional Patent Application Ser. No. 60/691,335 filed Jun. 16, 2005. This application is also related to U.S. Pat. No. 6,950,494 to Vija et al., issued Sep. 27, 2005 and assigned to the same assignee herein. The '494 patent is incorporated by reference herein in its entirety.

BACKGROUND OF THE INVENTION

1. Field of the Invention

This invention generally pertains to systems and methods for analyzing computed tomography data. More particularly, the present invention is directed to a method of converting computed tomography (CT) data to linear attenuation coefficient data for use in nuclear medicine, such as to compensate for attenuation in SPECT and PET imaging. The present invention is specifically directed to methods for automatically adjusting correction factors for linear attenuation coefficient maps based on a finite acquisition window width. The invention further enables consideration of multi-emission SPECT isotopes.

2. Description of the Related Art

Medical imaging falls into two distinct modalities or types. Transmission imaging refers to imaging such as X-ray imaging where the imaging source (e.g., X-ray) is external to the subject and is transmitted through the subject to a detector. Emission imaging refers to imaging where the imaging source (e.g., gamma-emitting radiopharmaceutical) is internal to the subject (as a result of injection or ingestion) and is emitted from the subject to a detector. Attenuation of source radiation occurs when the source radiation passes through the subject tissue, as a result of the subject absorbing or scattering some of the radiation photons. In general it is a simple matter to determine the attenuation of a discrete transmission source, since the amount of the external source being transmitted through the subject is known, and can be compared with the amount of radiation exiting the subject. However, measurement of attenuation in emission imaging is more difficult, because the accurate amount of emission source radiation being generated in the subject that results in a quantity of radiation being detected outside the subject cannot be measured directly.

Appropriate corrections for scatter and attenuation correction are prerequisites for quantitative nuclear medicine. X-ray CT image volumes can be used to derive Linear Attenuation Coefficient (LAC) maps ("mu-maps" or "µ-maps"), suitable for compensating for attenuation in single-photon-emission-computed-tomography (SPECT) and positron-emission-tomography (PET).

In general, a transmission scan is performed at an energy level other than the energy of the emission scan. Thus, the resulting attenuation map needs to be scaled to the actual emission energy of the scan, before it can be used to correct for attenuation in the emission reconstruction process. For source-based derived mu-maps, the conversion is simple because the discrete transmission and emission energies are known. For x-ray CT however, the transmission spectrum is continuous (and not discrete as it is the case for source-based methods of mu-map derivation), and, more importantly, depends upon the particular CT scanner and the attenuating body.

FIG. 1 shows that attenuation coefficients for different types of tissue depend on the energy of the photons, and can be grouped in essentially four groups, depending on their atomic number, Z: Air, soft tissue, bone, and iron, with iron representing a class of "Very High-Z" implants, such as surgical screws, hip-replacements, or other possible very high-Z materials in the body.

X-ray CT images are calibrated so that each voxel is measured in units of Hounsfield, usually defined as:

$$HU^{Material} = (\mu_T^{Material} - \mu_T^{Water}) / \mu_T^{Water} - \mu_T^{Air}) * 1000 \quad (1),$$

In this definition $HU^{Water}=0$ and $HU^{Air}=-1000$. Other definitions set $HU^{Vacuum}=-1000$. All clinically used CT scanners have to be calibrated to yield $HU^{Water}=0$ for water for all scan techniques.

In this definition $\mu_T^{Material}$ is the linear attenuation coefficient of a given material at an "effective" transmission energy T, and $\mu_T^{Water}$ is the linear attenuation coefficient of water at the same "effective" transmission energy T. The linear attenuation coefficients are "narrow beam" values, which are derived from primary photon counts only, and thus do not include any scattered photons (see also FIG. 4).

Because a CT scanner emits a continuous spectrum of x-rays, an "effective" transmission energy is not easily obtained, and usually involves actual measurement of the scan object penetrating radiation spectrum. The HU values are normalized for all scanners and protocols if the CT scanner for clinical practice has been properly set-up and calibrated, so that water always corresponds to HU=0 and air corresponds to HU=−1000 (it is noted that some definitions multiply by a factor of $2^{10}=1024$; such cases are included within the scope of the invention). All clinical CT scanners have to be calibrated using a vendor specific protocol to conform to this definition. However, there is no definition for densities greater than water. For instance, the same bone tissue may have different HU values when acquired with different CT scanners. The HU value of a bone specimen may even change depending on the surrounding amount of soft tissue and reconstruction parameters on the same CT scanner. Converting bone tissue accurately and adaptively to the patient is important because otherwise it may contribute largely to attenuation of emission energy.

Various approaches are known for converting CT values to linear attenuation coefficients, depending on the degree and type of approximation treating the continuous CT spectrum. These methods can be grouped in two major classes: Uniform scaling, and Non-uniform scaling.

In Uniform scaling, all pixels in the transmission slices are multiplied by the same factor K, where K is usually computed from the linear attenuation coefficient of water at the effective transmission-energy T $\mu_T^{Water}$ and emission-energy E $\mu_E^{Water}$:

$$K = \mu_E^{Water} / \mu_T^{Water} \quad (2)$$

This approach is accurate for soft tissues (low Z), since their attenuation properties are similar to water. In water, or other low-Z materials, Compton scattering is the dominant effect for clinically used emission energies, but for high-Z materials such as bone, the photoelectric absorption becomes the dominant effect. As a result, a scaling factor derived using water deviates considerably from a bone-derived scaling value. Thus, equation (2) provides inaccurate linear attenuation coefficients for materials more dense than water and soft tissue. The equation also assumes that an "effective" transmission-energy is known.

For a CT scan, the transmission energy can be only an "effective" transmission-energy, which essentially replaces the continuous transmission spectrum through the body with a mono-energetic "effective" transmission-energy. However, such an effective transmission-energy depends on the type of CT scanner, patient, and also on the CT reconstruction parameters. Examples of such methods are described in Kalki K., Brown, J. K., et al., "Myocardial Perfusion Imaging with a Correlated X-ray CT and SPECT System: An Animal Study", IEEE TNS, 43(3), 1996, pp. 2000-2007, 1996, which is incorporated herein by reference.

Non-Uniform Scaling Tissue method allows regions of the CT image volume to be defined as part of different classes of tissues ("segmentation"). Either each class of tissue is scaled from some "effective" transmission energy to the emission energy, or pixel values for each tissue type are replaced with the appropriate attenuation coefficients at the emission energy. Typical choices for tissue types include soft tissue, bone, lung and air. However, there are numerous problems with this approach. For example, this method does not take into account existing variations in tissues densities for the same tissue classes, it is limited to the errors of the segmentation routine, it may require an educated user to segment the data accurately, and it is not user-friendly.

Pixel-by-pixel conversion is an extension of the tissue typing approach. In this method, each pixel is scaled from CT units to linear attenuation coefficients. In principle, this method requires knowledge of the type of tissue for each pixel. This is often difficult because pixels may contain more than one tissue type ("partial volume"), or an educated user may be needed to identify the tissue type of each pixel (see, D. R. White, M. Fitzgerald, "Calculated attenuation and Energy Absorption Coefficients for ICRP Reference Man (1975) Organs and Tissues", Health Physics, 33, pp. 73-81, 1977, which is incorporated herein by reference). Therefore, this method suffers from similar problems.

Improved systems and methods for creating linear attenuation coefficient maps from CT image data that solve the foregoing problems are taught in the '494 patent incorporated by reference hereinabove, wherein a method is taught that adapts to patient specific data and the varying parameters of the CT scan and reconstruction, thereby eliminating the need for any additional calibrations, other than the clinically necessary, vendor specific CT scanner calibrations.

The '494 patent further teaches a method including the steps of receiving output pixel data from a CT device for a pixel of a CT image; comparing a value of the pixel data to a predetermined range; if the value is within the predetermined range, calculating a linear attenuation coefficient from the pixel data using a first function; if the value is outside the predetermined range, calculating the linear attenuation coefficient from the pixel data using a second function; and storing the calculated coefficient in a memory as part of a linear attenuation coefficient map.

While the above method takes into account the dependencies of linear attenuation coefficients on tissue type and photon energy, the method does not take into account variations in the energy window of SPECT data acquisitions. Further, in the case of multi-emission isotopes, the prior method uses a generalized estimation of the effective emission energy.

Therefore there exists a need in the art for improvements in generation of attenuation maps for nuclear medicine image reconstructions based on the use of anatomical image data, such as CT data, which take into account variations caused by variations in acquisition energy width and emission energy of the radioisotope used in the clinical imaging procedure.

SUMMARY OF THE INVENTION

In accordance with the foregoing and other objects, the present invention provides systems and methods for converting CT data to a linear attenuation coefficient map for use in nuclear medical image reconstruction.

According to one embodiment of the present invention, a method is provided for converting CT images obtained from an arbitrary clinical CT scanner to "mu-maps" wherein automatic adjustment is made of patient-specific linear attenuation coefficients for particular acquisition energy window settings.

According to another embodiment of the present invention, a method is provided for converting CT images obtained from an arbitrary clinical CT scanner to "mu-maps" wherein automatic adjustment is made of patient-specific linear attenuation coefficients for multi-emission gamma emitting isotopes.

With these and other objects, advantages and features of the invention that may become hereinafter apparent, the nature of the invention may be more clearly understood by reference to the following detailed description of the invention, the appended claims, and the drawings attached hereto.

BRIEF DESCRIPTION OF THE DRAWINGS

The invention will be described in detail with reference to the following drawings, in which like features are represented by common reference numbers and in which.

DETAILED DESCRIPTION OF THE PREFERRED EMBODIMENTS

Figure 1:
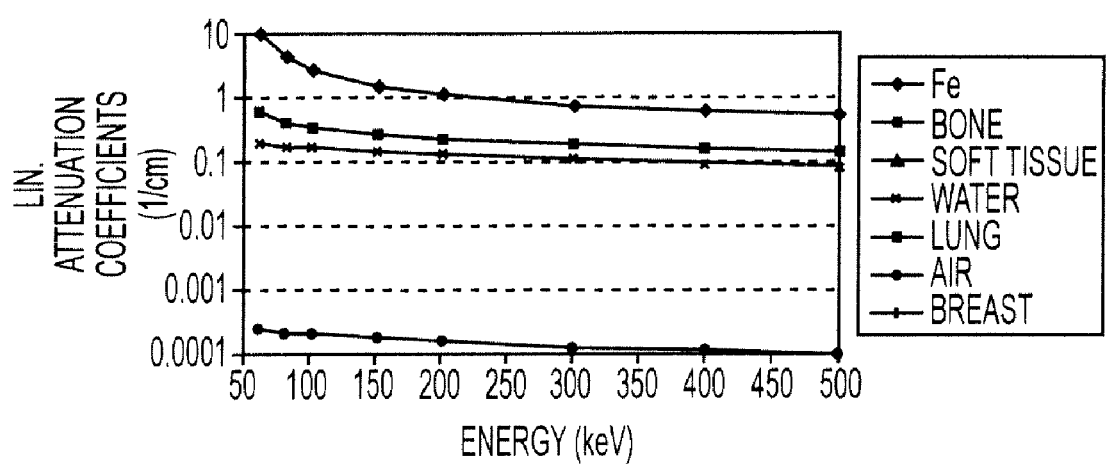
FIG. 1 shows linear attenuation coefficients for different types of tissue and their dependencies on the energy of the photons.
Figure 2:
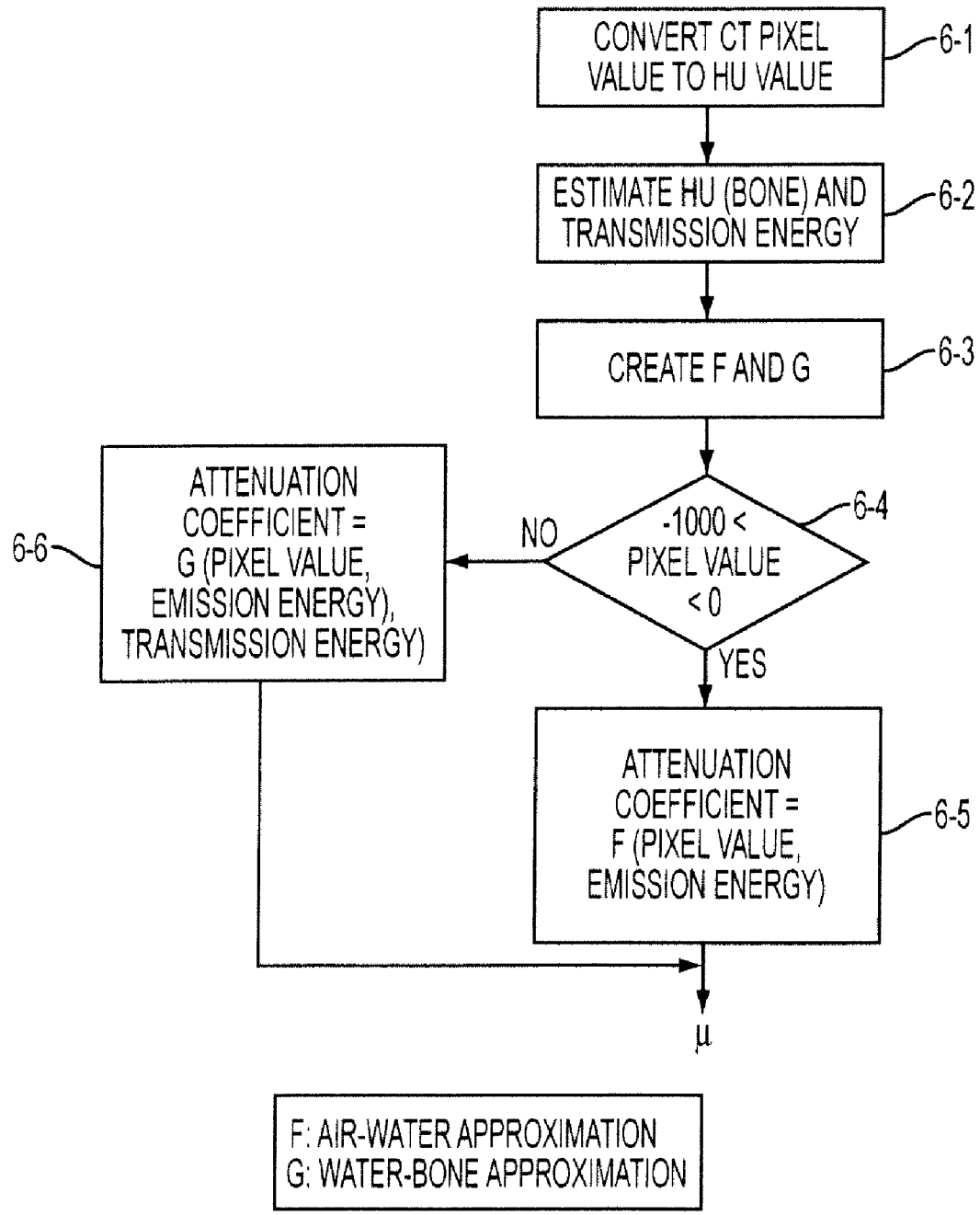
FIG. 2 is a flow diagram of a method for converting from HU to linear attenuation coefficients according to an embodiment of the present invention.

The basic concepts upon which the present invention builds are disclosed in U.S. Pat. No. 6,950,494 incorporated by reference hereinabove. As explained therein, FIG. 2 is a flow diagram of a method of generating linear attenuation correction factors $\mu$ also in accordance with the present invention. It will be understood by those skilled in the art that the following processes may be programmed onto central processor or computer, which may be coupled with a CT scanning device, or which may receive CT data in any fashion. Accordingly, a program written to perform the following may be stored conventionally in memory. Accordingly, the present invention is not limited to any particular system configuration.

Beginning with step 6-1, CT pixel values are converted to HU values. CT devices may output pixel data a number of ways. Typically, a device outputs data in a proprietary fashion that must be converted to HU. The conversion is usually provided by the vendor. For example, CT devices may output DICOM ("Digital Imaging and COmmunication in Medicine" standard) compliant data containing a header that defines the conversion from proprietary pixel data to HU. Obviously, if a CT device outputs pixel values as HU values, then the conversion is unity.

At step 6-2, HU (bone) and the effective transmission energy are estimated. In one embodiment of the present invention, a simple "numerical observer" replaces the educated human observer. However, it is to be noted that the present invention also applies to more sophisticated numerical observers, using e.g. Artificial Intelligence, data base scoring, statistical methods, etc. One implementation of such a "numerical observer" uses the histogram of the CT image volume to find the most common bone HU value at the given scan parameters in the CT image volume. This value is assigned to be $HU_T^{Bone}$, where the sub-script "T" indicates that this value is at some "effective" CT transmission energy. This "effective" CT transmission energy includes all possible effects that could influence the bone-HU, including effects from, e.g., the CT reconstruction filter.

Once the effective transmission energy is determined at step 6-2, conversion functions F and G are created at step 6-3. The energy dependence of the linear attenuation coefficient can be fitted by a double-power law, with coefficients a, b, c for energies below and above a transition energy $E_{TH}$:

$$\mu(E)=a_<E^{b_<}+c_< \text{ for } E \leq Eth;$$

$$\mu(E)=a_>E^{b_>}+c_> \text{ for } E \geq Eth;$$

At step 6-4, it is determined whether the pixel value is between −1000 (HU for air) and 0 (HU for water). If so, processing proceeds to step 6-5. If not, processing proceeds to step 6-6.

At step 6-5, air-soft tissue region is converted using a linear function F, calculated from the data points of air and water, for which the energy dependence is obtained from the above fit to the above double-power law. Because air and water values on the HU scale are independent of the transmission energy, this conversion is accurate.

At step 6-6, a conversion for all other values can then be calculated using the conversion function G for the Soft tissue-Bone region. Function G is approximated by a preferably linear fit to the data from soft-tissue and the identified bone tissue, with the constraint that the conversion function is continuous over the whole HU-range, i.e. F(HU=0)=G(HU=0).

Thus, values for U are generated from the pixel values of any x-ray CT imaging device. The generated μ-map may be used in nuclear medicine imaging, such as SPECT and PET.

Correction for Width of Finite Acquisition Energy Window

In accordance with one aspect of the present invention, the patient-specific linear attenuation coefficients μ are adjusted in accordance with the particular finite acquisition energy window for a nuclear medicine (e.g., SPECT) image data acquisition.

Figure 3:
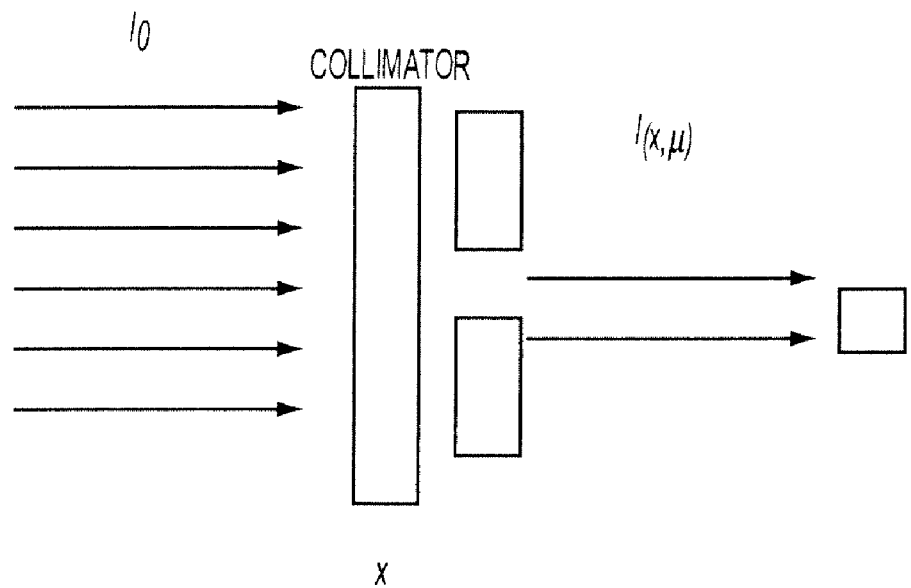
FIG. 3 is a diagram of a collimator showing "narrow beam" attenuation of initial flux.

Attenuation is the effect of detecting less photon flux due to the presence of an attenuating medium. If no medium is present the initial flux is denoted in the following as $I_o$ and in the presence of such a material it is denoted as I(x,μ), where x is the length of the traversed distance of the photons in the material with linear attenuation coefficient μ. The value I(x,μ) and $I_o$ are related by Beer's law: $I(x,\mu)=I_o e^{-\mu x}$ (see FIG. 3). The linear attenuation coefficient μ in this equation is assumed not to contain any scatter, and is referred to as the "narrow beam" linear attenuation coefficient.

In conventional practice, SPECT projection data always contains object scatter, due to necessary large size of the acquisition window, and thus, compensating for attenuation in a reconstruction with narrow beam attenuation values, may result in an over-correction, unless scatter is specifically addressed using some compensation scheme prior, during, or post reconstruction. One conventional practice to correct for this problem is to reduce the attenuation values by some factor. This factor depends on the energy of the nuclear medicine image and the acquisition window width (the wider acquisition window, the more scatter is collected, the lower the factor), which is often neglected. These correction factors are computed from a model using measurements, and a $X^2$-fit to characterize the factor for the two parameters (emission energy E and window width W) for all possible energies and window widths that could feasibly be used in clinical application and data acquisition.

Figure 4:
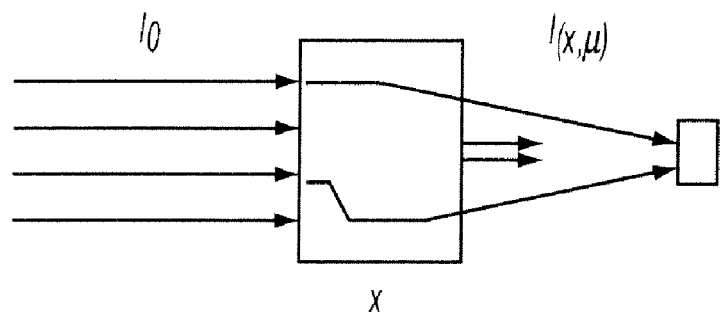
FIG. 4 is a diagram of a collimator showing "broad beam" attenuation of initial flux.

The difference between "narrow beam" and "broad beam" coefficients is that the first does not include any object scatter, and is the ideal case, whereas the latter does include object scatter. The nomenclature refers to the experimental set-up, where the beam is highly collimated before entering the detector, and thus is a "narrow" beam, or where it is not collimated and thus is a "broad" beam (see FIG. 4).

In clinical practice, narrow-beam conditions are not feasible, and it is therefore up to the conversion method and the SPECT image reconstruction method to compensate for the various physical conditions present during a clinical scan (i.e., "broad-beam conditions") in order to avoid possible image artifacts.

The data obtained in a nuclear image acquisition depends on multiple parameters, such as the number of acquisition energy windows and their boundaries, collimator type, scan orbit, and also the CT input data itself. Hereinafter, the discussion will be with respect to μ-maps derived from CT (as described in the incorporated '494 patent); however the inventive concepts may be applied to anatomical data converted to a μ-map, such as an MR-derived μ-map.

In accordance with a first embodiment of the invention, it is assumed that the broad-beam linear attenuation coefficient $\mu_{bb}(E,W,C)$ does not depend on the patient but instead can be derived by a simple global scaling of the narrow-beam coefficient $\mu_{nb}(E)$ by a broad-beam correction factor $K_{bb}(E,W,C)$, such that:

$$\mu_{bb}(E,W,C)=\mu_{nb}(E)*K_{bb}(E,W,C)$$

where E denotes the emission energy, W denotes the energy window width in percent of center energy in keV, and C denotes the collimator angular resolution.

The dependency of $K_{bb}$ on E and W further can be approximated as a double polynomial:

$$K_{bb}(E, W) = \sum_i \left( \sum_j a_{ij} E^j \right) W^i \qquad (3)$$

although any function $f \subset C^1$ which is an appropriate fit to measured data would be acceptable, of which Equation (3) is but one example.

The collimator dependency can be either parameterized by collimator angular resolution, or based discretely as a function of collimator type, which is chosen herein, i.e., $K_{bbC}(E,W)=K_{bb}(E,W,C)$, with C as a discrete index. The final approximation is that the broad-beam factor is measured and parameterized for water or soft tissue only. Of course, the broad-beam factor also can be expanded to include more tissue types, such that the correction factor would also depend upon the tissue class $T_j$ at pixel j, i.e., $K_{bb}(E,W,C,T_j)$. The values $a_{ij}$ have been determined for LEHR and LEAP collimators based on data for various emission energies and acquisition window widths. The broad-beam correction factors can be stored in the DICOM header of the μ-map. Depending on the SPECT reconstruction method and whether scatter compensation is used or not, the broad-beam correction factors may be applied or not applied to the attenuation coefficients.

Estimation of Effective Emission Energy from Multiple Energy Emission Data

Figure 5:
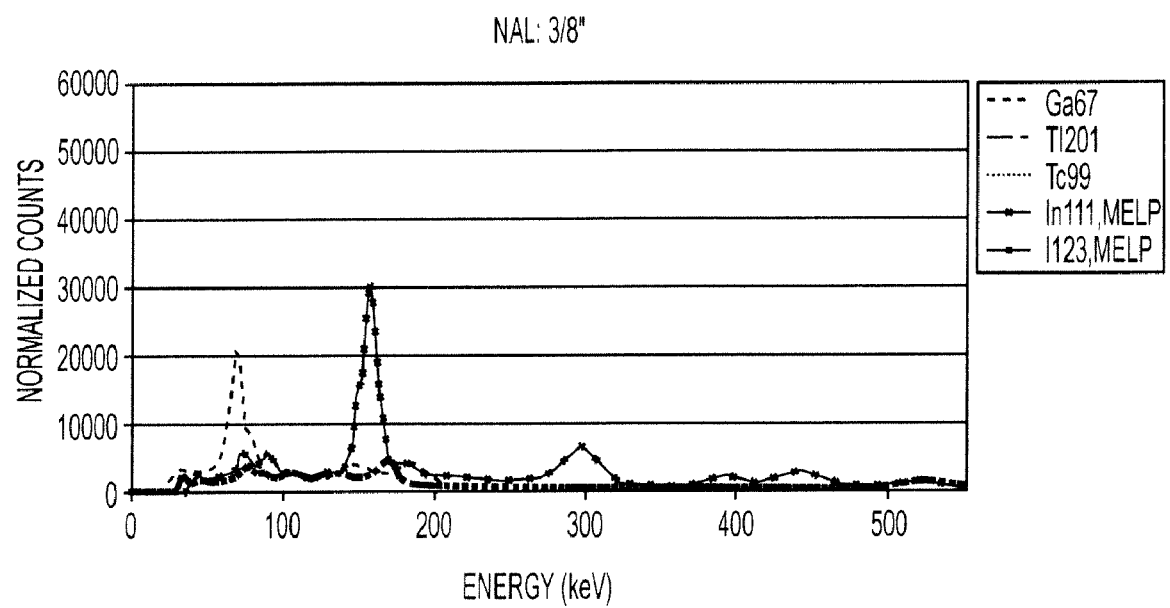
FIG. 5 is a graph showing an emission spectrum as detected by a scintillation crystal of various multi-emission radioisotopes usable in accordance with the present invention.

Some clinical applications require the use of isotopes such as $^{201}$Tl, $^{111}$In or $^{67}$Ga, having more than one emission energy, which could be used for emission imaging. Thus the SPECT acquisition may be performed with multiple acquisition windows summed into one projection image to as to improve the statistical quality, as is sometimes done in clinical practice. Here, the conversion problem can be generalized to a conversion from the effective transmission energy to an effective emission energy, wherein a discrete spectrum can be replaced by one "effective" emission energy value. In other words, the attenuation map has to be scaled to a single effective energy value that best approximates the effective attenuation of the discrete emission spectrum that is detected by the scintillation detector, as shown for example in FIG. 5.

The general concept therefore is that the effective energy is the single energy that best approximates or describes the emission spectrum, such that attenuation resulting from that effective energy is as close as possible to the attenuation resulting from the emission spectrum as photons thereof pass through material (e.g., water) of a certain thickness D. Here, the effective energy is computed only for soft tissue or water, as soft tissue containing high amounts of water is the predominant tissue of the body.

The method to calculate the appropriate effective emission energy $E_{eff}$ can use a weighted $X^2$ fit, which can include n windows, for the broad-beam attenuation coefficients $\mu_w$ for water at the emission energies $E_j$. The center of the effective energy window can be approximated using the narrow-beam values together with branching ratios (e.g., from isotope decay tables), while the width of the effective energy window can be approximated with broad-beam values together with abundance ratios, by essentially inverting Equation (3). Thus, the effective attenuation correction factor Peff can be determined as:

$$\mu_{eff} = \min_{\mu_{eff}, I_0^{eff}} \arg \left[ \sum_{i=1}^{k} \frac{\left[\left(\sum_{j=1}^{n} I_0^j e^{-\mu_W(E_j)D}\right) - I_0^{eff} e^{-\mu_W(E_{eff})D}\right]^2}{\sum_{j=1}^{n} \sigma_j^2} \right]; \quad (4)$$

$$E_{eff} = \left(\frac{(\mu_{eff} - c)}{a}\right)^{1/b},$$

where appropriate coefficients a, b, c are provided for the fitting function $\mu = aE^b + c$.

Each emission energy has a certain probability of occurrence, from which is determined the branching ratios of the various possible decay channels. However, effective branching or abundance ratios must be computed from the emission spectra, taking into account the individual acquisition energy windows and various scintillation detector and/or crystal effects at the various energies, so as to reflect the actual acquisition of clinical data.

The abundance ratio can be computed from an acquired emission spectrum of the radioisotope at issue under actual SPECT imaging conditions (i.e., collimator type, scintillation crystal thickness, etc), and is represented as:

$$I_0^j = \frac{N_j}{\sum_{k=1}^{m} N_k};$$

-continued $$N_k = \int_{E=E_{low}:=E_c-\Delta/2}^{E_{high}:=E_c+\Delta/2} n(E)dE \approx \sum_{E=E_{low}}^{E_{high}} n(E_i)\partial E$$

where $N_k$ denotes the counts in the window k, and $E_c$ is the center of the energy window with width $\Delta$. In order to maintain consistency between single emission $\mu$-maps, which have a single emission energy window boundary stored in the header file, an effective energy $\mu$-map also needs an effective acquisition window width. The center energy is computed using the branching ratios (determined as per above) and narrow-beam attenuation coefficient values.

The effective energy window width is computed by solving Equation (4) using the abundance ratio and broad-beam attenuation coefficient values for each peak $E_i$. The broad-beam values are computed from the narrow-beam values by multiplication with the appropriate correction factor $K_{bb}(E_i, W_i)$ for each $E_i$ and $W_i$. The resulting $\mu_{eff}$ is now an effective broad-beam attenuation coefficient value. The ratio between this value and the narrow-beam value as computed by Equation (4) using center energy, yields an effective broad-beam compensation factor, which can be solved for the effective energy window width using Equation (3).

Thus, the invention has been described in connection with what are presently considered to be the most practical and preferred embodiments. However, it is to be understood that the invention is not to be limited to the disclosed embodiments, but, on the contrary, is intended to cover various modifications and equivalent arrangements included within the spirit and scope of the appended claims.

In particular, the invention can be applied to mu-maps derived from any anatomical imaging modality, such as MR, and is not limited to CT data. Further, the assumption of patient-independence of the broad-beam factors can be eliminated if the anatomical data is used to obtain local broad-beam correction factors. Then, based on tissue type, which can be inferred from the anatomical information in the anatomical data, local broad-beam correction factors $K_{bb}(E,W,C,r)$ at locations r can be used. A measurement with a matrix phantom would have to be repeated for numerous tissue types, which could be approximated based on common standards (e.g. ICRP) in plastic equivalents such as Gammex tissue equivalents.

What is claimed is:

1. A method of correcting a linear attenuation coefficient map obtained from anatomical image data, said map being used in nuclear medical image reconstruction, comprising the steps of:
    obtaining a set of linear attenuation coefficient correction factors based on different acquisition energy windows used for acquisition of nuclear medical projection data, wherein each of said correction factors are computed based on an emission energy of a radioisotope, and a width of an energy window used to detect radiation photons emitted from said radioisotope;
    storing said set of linear attenuation coefficient correction factors together with said map; and
    applying a particular stored linear attenuation coefficient correction factor to a linear attenuation coefficient retrieved from said map for correction of projection data used in a reconstruction process, according to the emission energy of a radioisotope used for generation of said projection data and a width of an acquisition energy window used to acquire said projection data,
    wherein said set of linear attenuation coefficient correction factors are computed based additionally on at least one of a collimator type and collimator angular resolution.

2. The method of claim 1, wherein said linear attenuation coefficient map is obtained from CT data.

3. The method of claim 1, wherein said projection data is SPECT data.

4. The method of claim 1, wherein said set of linear attenuation coefficient correction factors are stored in a DICOM header of said map.

5. The method of claim 1, wherein said linear attenuation coefficient correction factors are approximated as:

$$K_{bb}(E, W) = \sum_i \left( \sum_j a_{ij} E^j \right) W^i,$$

where E denotes the emission energy and W denotes the energy window width as a percentage of center energy.

6. The method of claim 1, further comprising the steps of:
estimating an effective emission energy of a multi-emission radioisotope using a weighted $x^2$ fit for linear attenuation coefficients at each emission energy of said multi-emission radioisotope;
estimating an effective acquisition energy window width using an abundance ratio computed based on counts of an acquired emission spectrum of said multi-emission radioisotope in each of a number of energy windows corresponding to each emission energy of said multi-emission radioisotope, center energies of each of said number of energy windows, and widths of each of said number of energy windows; and
using said estimated effective emission energy and effective acquisition energy window to obtain a set of linear attenuation coefficient correction factors for said multi-emission radioisotope.

7. The method of claim 6, wherein said multi-emission radioisotope is $^{111}$In.

8. The method of claim 6, wherein said multi-emission radioisotope is $^{67}$Ga.

9. The method of claim 6, wherein said abundance ratio is represented as:

$$I_0^j = \frac{N_j}{\sum_{k=1}^m N_k};$$

$$N_k = \int_{E=E_{low}:=E_c-\Delta/2}^{E_{high}:=E_c+\Delta/2} n(E)\,dE \approx \sum_{E=E_{low}}^{E_{high}} n(E_i)\partial E.$$

10. The method of claim 6, wherein said multi-emission radioisotope is $^{201}$Tl.

11. The method of claim 1, wherein said linear attenuation coefficient map is obtained comprising the steps of:
receiving output pixel data from a CT device for a pixel of a CT image;
comparing a value of the pixel data to a predetermined range;
if said value is within said predetermined range, calculating a linear attenuation coefficient from said pixel data using a first function;
if said value is outside said predetermined range, calculating said linear attenuation coefficient from said pixel data using a second function; and
storing said calculated coefficient in a memory as part of said linear attenuation coefficient map.

12. A computer program product, residing on a computer readable medium, comprising computer executable instructions for causing a computer to perform the following functions for correcting a linear attenuation coefficient map obtained from anatomical image data, said map being used in nuclear medical image reconstruction:
obtaining a set of linear attenuation coefficient correction factors based on different acquisition energy windows used for acquisition of nuclear medical projection data, wherein each of said correction factors are computed based on an emission energy of a radioisotope, and a width of an energy window used to detect radiation photons emitted from said radioisotope;
storing said set of linear attenuation coefficient correction factors together with said map; and
applying a particular stored linear attenuation coefficient correction factor to a linear attenuation coefficient retrieved from said map for correction of projection data used in a reconstruction process, according to the emission energy of a radioisotope used for generation of said projection data and a width of an acquisition energy window used to acquire said projection data,
wherein said set of line attenuation coefficient correction factors are computed based additionally on at least one of a collimator type and collimator angular resolution.

13. The computer program product of claim 12, wherein said linear attenuation coefficient map is obtained from CT data.

14. The computer program product of claim 12, wherein said projection data is SPECT data.

15. The computer program product of claim 12, wherein said set of linear attenuation coefficient correction factors are stored in a DICOM header of said map.

16. The computer program product of claim 12, wherein said linear attenuation coefficient correction factors are approximated as:

$$K_{bb}(E, W) = \sum_i \left( \sum_j a_{ij} E^j \right) W^i,$$

where E denotes the emission energy and W denotes the energy window width as a percentage of center energy.

17. The computer program product of claim 12, further comprising computer executable instructions for:
estimating an effective emission energy of a multi-emission radioisotope using a weighted $x^2$ fit for linear attenuation coefficients at each emission energy of said multi-emission radioisotope;
estimating an effective acquisition energy window width using an abundance ratio computed based on counts of an acquired emission spectrum of said multi-emission radioisotope in each of a number of energy windows corresponding to each emission energy of said multi-emission radioisotope, center energies of each of said number of energy windows, and widths of each of said number of energy windows; and
using said estimated effective emission energy and effective acquisition energy window to obtain a set of linear attenuation coefficient correction factors for said multi-emission radioisotope.

18. The computer program product of claim 17, wherein said abundance ratio is represented as:

$$I_0^j = \frac{N_j}{\sum_{k=1}^m N_k};$$

$$N_k = \int_{E=E_{low}:=E_c-\Delta/2}^{E_{high}:=E_c+\Delta/2} n(E)\,dE \approx \sum_{E=E_{low}}^{E_{high}} n(E_i)\partial E.$$

* * * * *